United States Patent
Hoffman et al.

(10) Patent No.: US 7,382,854 B2
(45) Date of Patent: Jun. 3, 2008

(54) CT DETECTOR HAVING A SEGMENTED OPTICAL COUPLER AND METHOD OF MANUFACTURING SAME

(75) Inventors: David M. Hoffman, New Berlin, WI (US); Michael F. Hoge, Waukesha, WI (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 11/626,181

(22) Filed: Jan. 23, 2007

(65) Prior Publication Data
US 2007/0116174 A1    May 24, 2007

Related U.S. Application Data (60) Continuation of application No. 11/423,277, filed on Jun. 9, 2006, now Pat. No. 7,173,998, which is a continuation of application No. 11/163,973, filed on Nov. 4, 2005, now Pat. No. 7,084,404, which is a division of application No. 10/908,209, filed on May 2, 2005, now Pat. No. 7,064,334, which is a continuation of application No. 10/249,052, filed on Mar. 12, 2003, now Pat. No. 6,933,504.

(51) Int. Cl.
*A61B 6/00* (2006.01)
(52) U.S. Cl. .................... 378/19; 250/370.11
(58) Field of Classification Search ............ 378/4, 378/19, 98.8, 145–147, 154; 250/370.08, 250/370.09, 370.11
See application file for complete search history.

(56) References Cited

U.S. PATENT DOCUMENTS

| | | | |
|---|---|---|---|
| 4,234,792 A | 11/1980 | DeCou et al. | |
| 4,694,177 A | 9/1987 | Akai | |
| 4,982,096 A | 1/1991 | Fujii et al. | |
| 5,038,042 A | 8/1991 | Hansen et al. | |
| 5,276,328 A | 1/1994 | Yoshida et al. | |
| 5,506,409 A | 4/1996 | Yoshida et al. | |
| 5,712,483 A | 1/1998 | Boone et al. | |
| 5,866,908 A | 2/1999 | Novak | |
| 6,075,835 A | 6/2000 | Acharya et al. | |
| 6,091,795 A | 7/2000 | Schafer et al. | |
| 6,292,529 B1 | 9/2001 | Marcovici et al. | |
| 6,298,113 B1 | 10/2001 | Duclos et al. | |
| 6,344,649 B2 | 2/2002 | Riedner et al. | |
| 6,362,481 B1 | 3/2002 | Warren | |
| 6,393,092 B1 | 5/2002 | Yoshida | |
| 6,473,486 B2 | 10/2002 | Hoffman | |
| 6,480,562 B2 | 11/2002 | Jiang et al. | |
| 6,480,563 B2 | 11/2002 | Hoffman et al. | |
| 6,534,773 B1 | 3/2003 | Iwanczyk et al. | |
| 6,553,092 B1 | 4/2003 | Mattson et al. | |

(Continued)

Primary Examiner—Courtney Thomas
(74) Attorney, Agent, or Firm—Ziolkowski Patent Solutions Group, SC (57) ABSTRACT

The present invention is a directed to a CT detector for a CT imaging system that incorporates a segmented optical coupler between a photodiode array and a scintillator array. The segmented optical coupler also operates as a light collimator which improves the light collection efficiency of the photodiode array. The segmented optical coupler is defined by a series of reflector elements that collectively form a plurality of open cells. The open cells form light transmission cavities and facilitate the collimation of light from a scintillator to a photodiode. The cavities may be filled with optical epoxy for sealing to the photodiode array.

21 Claims, 9 Drawing Sheets

U.S. PATENT DOCUMENTS

| | | |
|---|---|---|
| 6,654,443 B1 | 11/2003 | Hoffman |
| 6,704,391 B2 | 3/2004 | Hoffman et al. |
| 6,717,150 B2 | 4/2004 | Hoffman |
| 6,775,348 B2 | 8/2004 | Hoffman |
| 6,859,514 B2 | 2/2005 | Hoffman |
| 6,947,517 B2 * | 9/2005 | Hoffman ...................... 378/19 |
| 2003/0150994 A1 | 8/2003 | Freund et al. |

* cited by examiner

CT DETECTOR HAVING A SEGMENTED OPTICAL COUPLER AND METHOD OF MANUFACTURING SAME

CROSS REFERENCE TO RELATED APPLICATIONS

The present application is continuation of and claims priority of U.S. Ser. No. 11/423,277 filed Jun. 9, 2006, which is a continuation of and claims priority of U.S. Ser. No. 11/163,973 filed Nov. 4, 2005, now U.S. Pat. No. 7,084,404, which is a divisional of and claims priority of U.S. Ser. No. 10/908,209 filed May 2, 2005, now U.S. Pat. No. 7,064,334, which is a continuation of and claims priority of U.S. Ser. No. 10/249,052 filed Mar. 12, 2003, now U.S. Pat. No. 6,933,504.

BACKGROUND OF THE INVENTION

The present invention relates generally to diagnostic imaging and, more particularly, to a CT detector having a segmented or non-contiguous optical coupler and method of manufacturing same. Additionally, the segmented optical coupler operates as a light collimator integrally formed between the scintillators and photodiodes of the detector.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

"Cross talk" between detector cells of a CT detector is common. "Cross talk" is generally defined as the communication of data between adjacent cells of a CT detector. Generally, cross talk is sought to be reduced as cross talk leads to artifact presence in the final reconstructed CT image and contributes to poor spatial resolution. Typically, four different types of cross talk may result within a single CT detector. X-ray cross talk may occur due to x-ray scattering between scintillator cells. Optical cross talk may occur through the transmission of light through the reflectors that surround the scintillators. Known CT detectors utilize a contiguous optical coupling layer(s), typically epoxy, to secure the scintillator array to the photodiode array. Cross talk, however, can occur as light from one cell is passed to another through the contiguous layer. Electrical cross talk can occur from unwanted communication between photodiodes. Of the above types of cross talk, cross talk though the contiguous optical coupler layer(s) is generally considered a major source of cross talk in the CT detector.

Therefore, it would be desirable to design a CT detector having improved optical coupling between the scintillator array and photodiode array to reduce cross talk in the CT detector and improve spatial resolution of the final reconstructed image.

BRIEF DESCRIPTION OF THE INVENTION

The present invention is a directed to a CT detector for a CT imaging system that overcomes the aforementioned drawbacks. The CT detector incorporates a gridded light collimator between a photodiode array and a scintillator array. The light collimator improves the light collection efficiency of the photodiode array and may be formed of reflector material so as to reduce cross talk within the detector. Each gridded collimator is defined by a series of reflector elements that collectively form a plurality of open cells. The open cells form light transmission cavities and facilitate the collimation of light from a scintillator to a photodiode. The cavities may be filled with optical epoxy for sealing to the photodiode array or scintillator array thereby avoiding the drawbacks associated with contiguous optical coupler layers.

Therefore, in accordance with the present invention, a CT detector includes a plurality of scintillators arranged in an array to receive x-rays and output light in response to the received x-rays. A plurality of light detection elements are arranged in an array dimensionally similar to the scintillator array and are configured to detect light from the scintillators. A non-contiguous optical coupler is then used to secure the plurality of scintillators to the plurality of light detection elements.

According to another aspect of the present invention, a CT system includes a rotatable gantry having a bore centrally disposed therein and a table movable fore and aft through the bore and configured to position a subject for CT data acquisition. A high frequency electromagnetic energy projection source is positioned within the rotatable gantry and configured to project high frequency electromagnetic energy toward the subject. The CT system further includes a detector array disposed within the rotatable gantry and configured to detect high frequency electromagnetic energy projected by the projection source and impinged by the subject. The detector array includes a plurality of scintillators arranged in a scintillator array as well as a plurality of photodiodes arranged in a photodiode array. A light collimator having a plurality of light transmission cavities is disposed between the scintillator array and the photodiode array.

In accordance with a further aspect of the present invention, a method of CT detector manufacturing includes the steps of forming a scintillator array having a plurality of scintillators and forming a photodiode array having a plurality of photodiodes. An open-celled collimator is then deposited between the arrays. The resulting assembly is then secured to one another.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
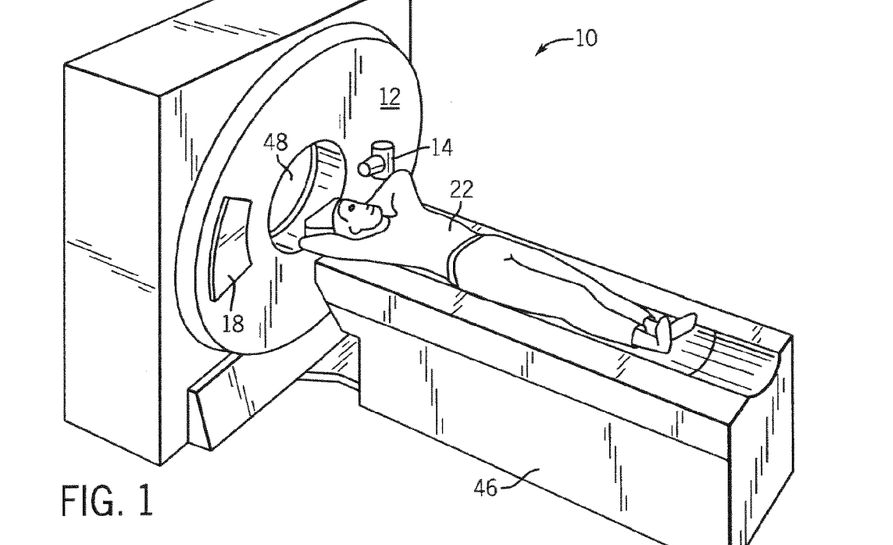
FIG. 1 is a pictorial view of a CT imaging system.
Figure 2:
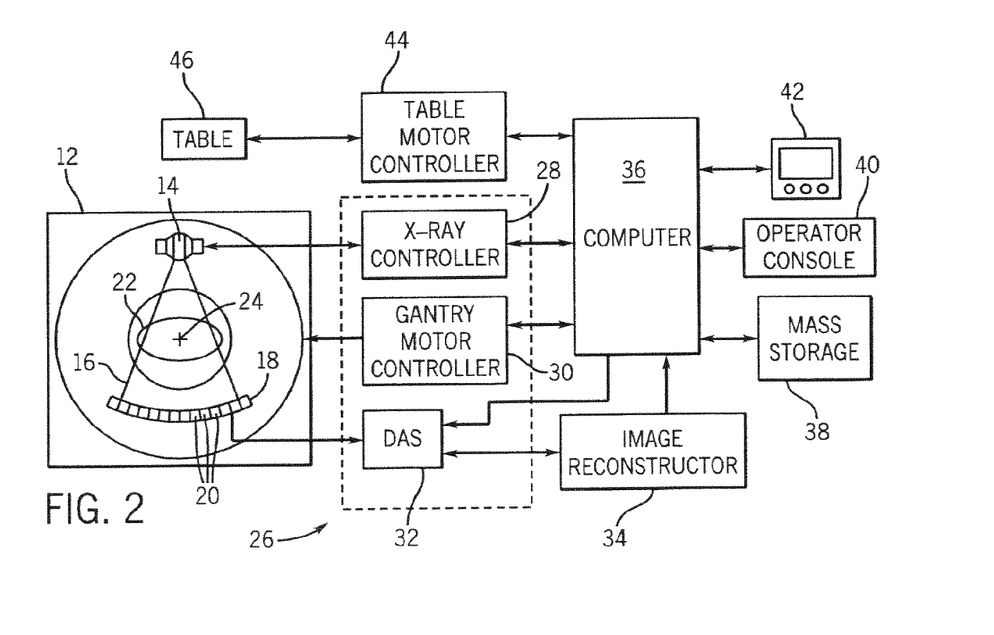
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Figures 3, 4:
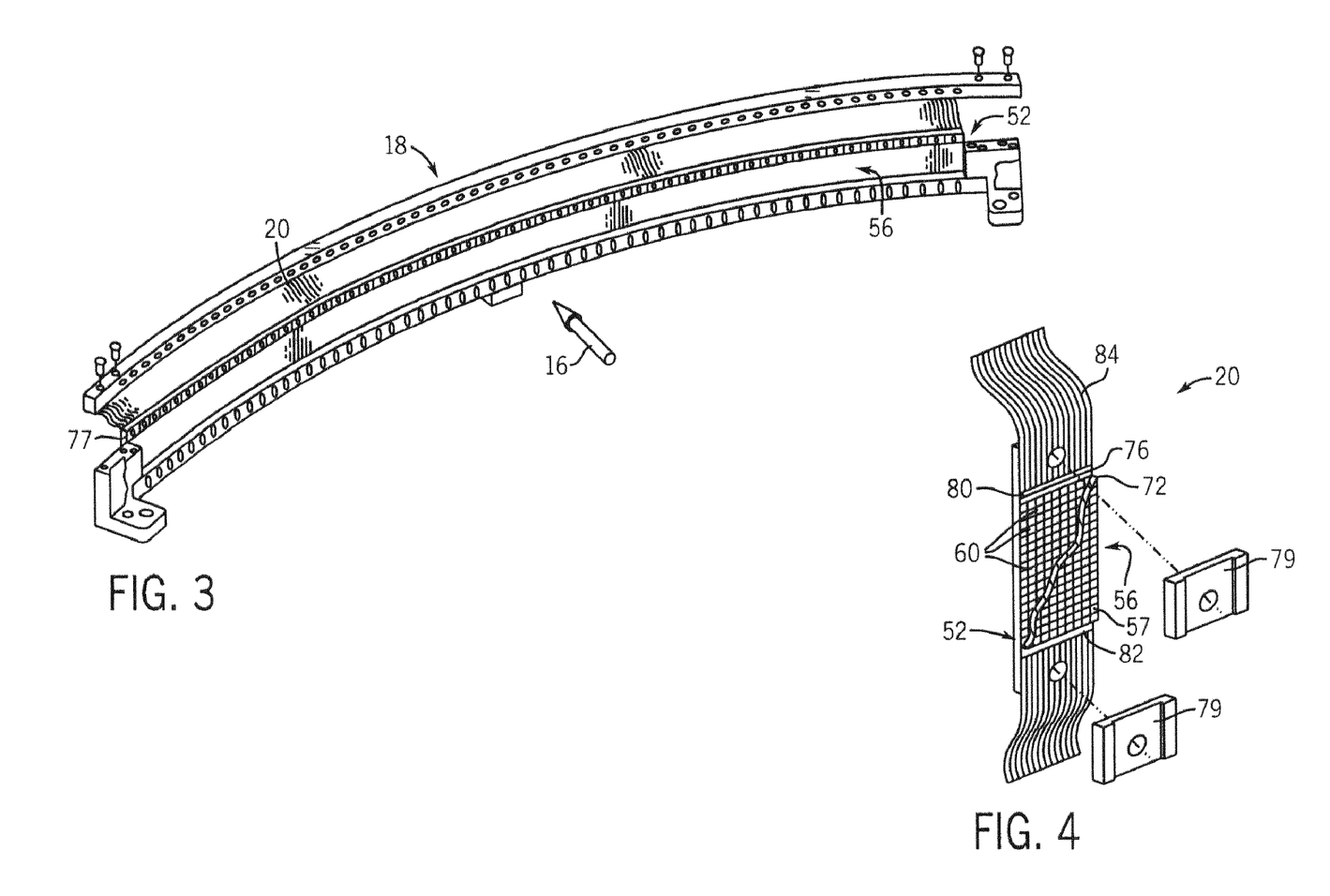
FIG. 3 is a perspective view of one embodiment of a CT system detector array.
FIG. 4 is a perspective view of one embodiment of a detector.

As shown in FIGS. 3 and 4, detector array 18 includes a plurality of scintillators 57 forming a scintillator array 56. A collimator (not shown) is positioned above scintillator array 56 to collimate x-ray beams 16 before such beams impinge upon scintillator array 56.

In one embodiment, shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12.

Switch arrays 80 and 82, FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective photodiodes 60 and a number of output leads electrically connected to DAS 32 via a flexible electrical interface 84. Particularly, about one-half of photodiode outputs are electrically connected to switch 80 with the other one-half of photodiode outputs electrically connected to switch 82. Additionally, a reflector layer (not shown) may be interposed between each scintillator 57 to reduce light scattering from adjacent scintillators. Each detector 20 is secured to a detector frame 77, FIG. 3, by mounting brackets 79.

Switch arrays 80 and 82 further include a decoder (not shown) that enables, disables, or combines photodiode outputs in accordance with a desired number of slices and slice resolutions for each slice. Decoder, in one embodiment, is a decoder chip or a FET controller as known in the art. Decoder includes a plurality of output and control lines coupled to switch arrays 80 and 82 and DAS 32. In one embodiment defined as a 16 slice mode, decoder enables switch arrays 80 and 82 so that all rows of the photodiode array 52 are activated, resulting in 16 simultaneous slices of data for processing by DAS 32. Of course, many other slice combinations are possible. For example, decoder may also select from other slice modes, including one, two, and four-slice modes.

Figure 5:
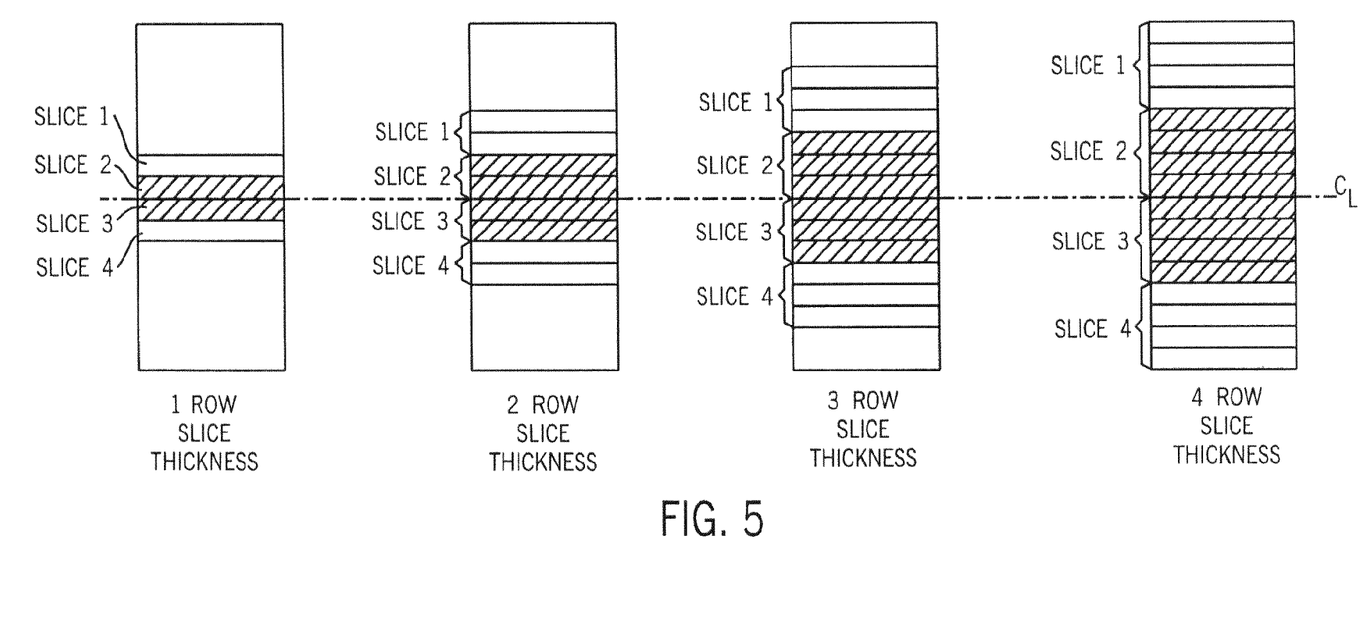
FIG. 5 is illustrative of various configurations of the detector in FIG. 4 in a four-slice mode.

As shown in FIG. 5, by transmitting the appropriate decoder instructions, switch arrays 80 and 82 can be configured in the four-slice mode so that the data is collected from four slices of one or more rows of photodiode array 52. Depending upon the specific configuration of switch arrays 80 and 82, various combinations of photodiodes 60 can be enabled, disabled, or combined so that the slice thickness may consist of one, two, three, or four rows of scintillator array elements 57. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

Figure 6:
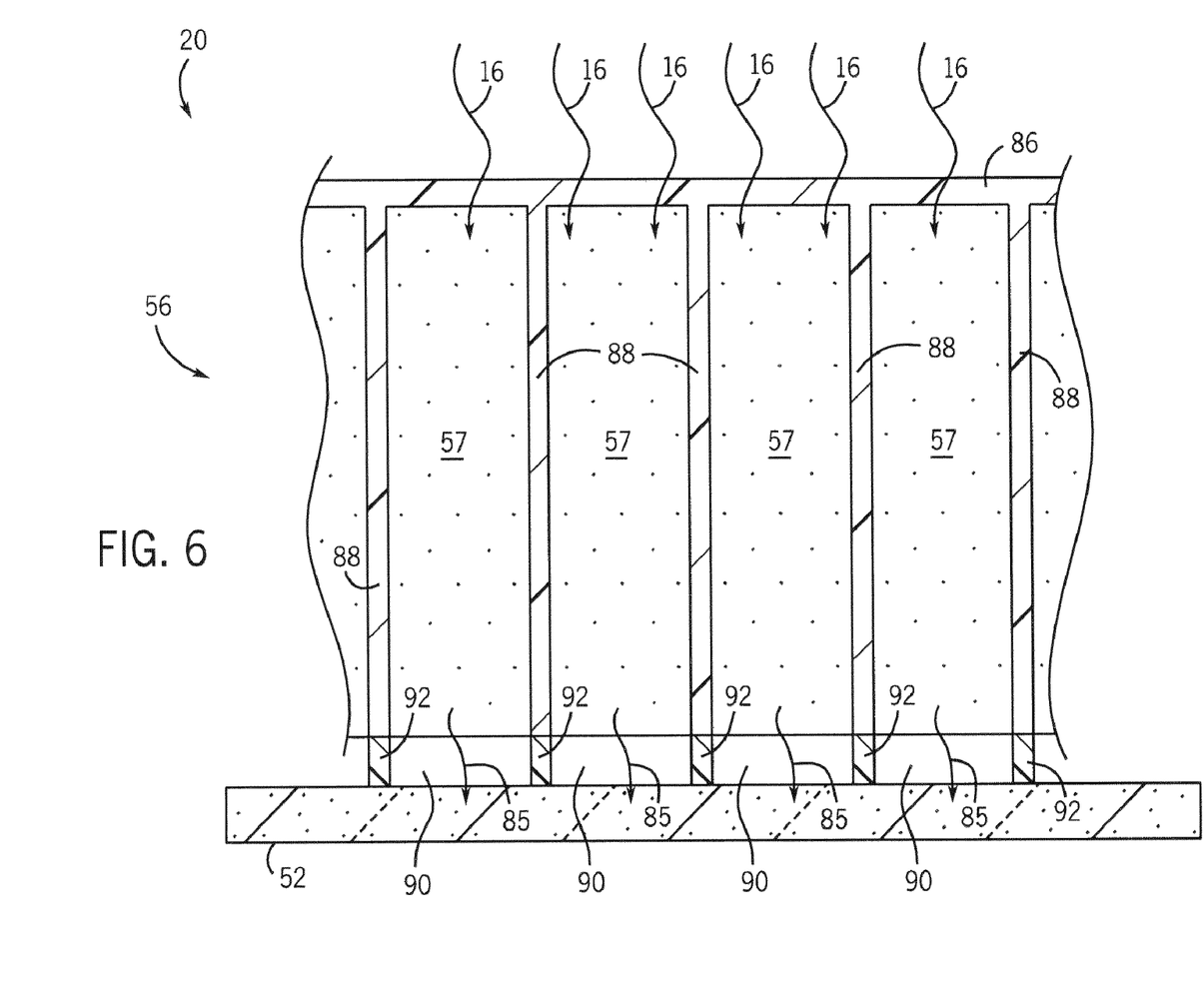
FIG. 6 is a schematic of a cross-section of a CT detector in accordance with the present invention.

Referring now to FIG. 6, a schematic of a cross-section of a CT detector 20 is shown. As discussed above, detector 20 includes a scintillator array 56 defined by a plurality of scintillators 57. Each of the scintillators is designed to generate a light output 85 in response the reception of x-rays 16. A reflector layer 86 coats the x-ray reception surface of the scintillators to improve light collection efficiency of the photodiodes. The reflector layer 86 is composed of a material that allows x-rays projected from a projection source to pass through and reflects light generated by the scintillators back toward the photodiodes. The reflector layer is integrated with a series of reflector elements 88 that extend between adjacent scintillators 57 as a reflector wall. The reflector elements 88 are designed to prevent light scattering and/or reduce x-ray scattering between scintillators.

CT detector 20 is constructed such that a light cavity 90 extends between each photodiode and scintillator. The light cavity may be constructed in accordance with a number of fabrication techniques as will be described with respect to FIGS. 7-10 and is defined by cavity elements or plates 92. Plates 92 are preferably formed of a reflector material similar to that used to form reflector elements 88. Additionally, plates 92 have a width similar to the width of the reflector elements 88. Preferably, plates 92 are formed during the formation of reflector elements 88, as will be described with respect to FIG. 7. As such, plates 92 extend from reflector elements to the light detection surface of the photodiode array.

Plates 92 are constructed to form light transmission cavities 90 and, as such, operate as an inner-cell light collimator. Plates 92 are designed to eliminate light cross talk between scintillators thereby collimating light toward the light detection surfaces of the photodiode array. Further, plates 92 may be coated with an optical coupling film or resin so as to secure the plates to the photodiode array. Alternately, the plates may be bonded to the surface of the photodiode array. In a further embodiment, each of the light transmission cavities 90 is filled with an optical epoxy similar to the epoxy used in a contiguous epoxy layer. The optical epoxy operates as adhesive to connect the photodiode array to the scintillator array. With the presence of reflector plates 92, the drawbacks associated with contiguous optical layer cross talk are avoided. While epoxy may be used to secure the arrays to one another, other composites and materials such as thermoplastics may be used and are within the scope of the invention.

Figure 7:
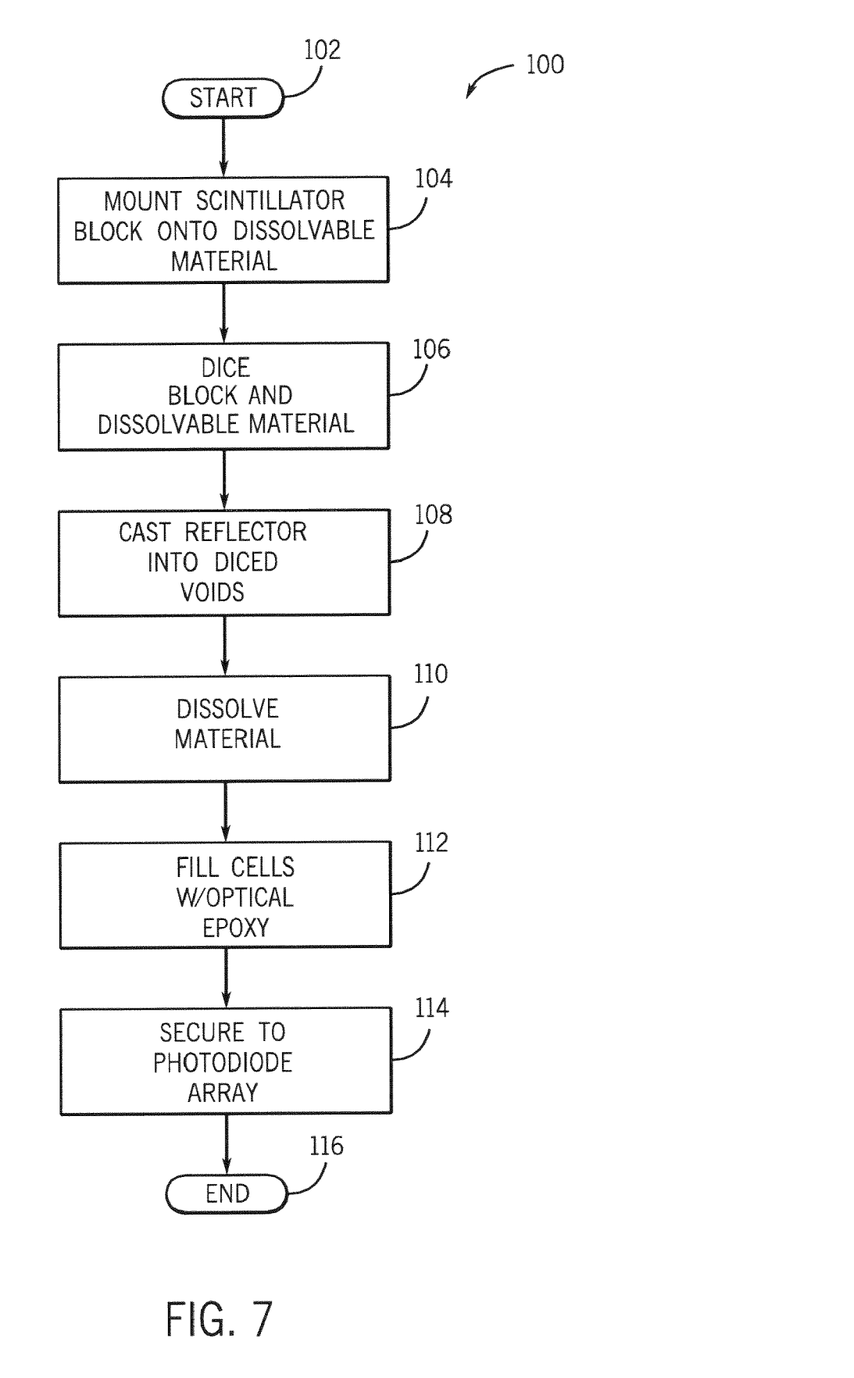
FIGS. 7-10 set forth steps of various techniques of manufacturing a CT detector in accordance with the present invention.

Referring now to FIG. 7, steps for a technique of manufacturing a CT detector similar to that described with respect to FIG. 6 are shown. The steps illustrated may be carried out by a labor intensive process, a fully automated, computer driven process, or a combination thereof. Technique 100 begins at 102 with the assimilation of products, personnel and the like for CT detector fabrication. That achieved during this step may vary but, at a minimum, should include the preparation of a scintillator block. The scintillator block is then mounted onto a dissolvable material 104. The scintillator block and dissolvable material are then diced or cut at 106. Once cut, either along one or two dimensions, a plurality of scintillator cells uniformly spaced from one another results. Reflector material is then cast at 108 in the voids created between the scintillator cells as a result of the dicing process. The reflector material should be cast such that the interface between scintillators is completely filled as is the interface between adjacent portions of the dissolvable material. The cast reflector material is then allowed to cure and undergoes any additional processing to insure proper reflectivity and the like. Once the cast reflector material has cured, the dissolvable material is dissolved at 110. The process for dissolving the material depends on the type of dissolvable material used. For example, the dissolvable material may be placed in a wash and chemically dissolved or heated at a specified temperature to, in essence, "melt" away the dissolvable material. After the dissolving process is complete, a scintillator array with an integrated cast reflector results. Of particular note is that each reflector element between the scintillators extends beyond the scintillator, i.e. has a greater length than the scintillators. The portion of the reflector that extends beyond the scintillator operates as a reflector plate as described above. The open cells that result between reflector plates define a light transmission cavity and are filled with optical epoxy at 112. The optical epoxy permits the transmission of light between scintillator and photodiode while simultaneously creating an adhesion interface for coupling the scintillator to the photodiode. As such, the photodiode array and scintillator array are coupled to one another at 114. This portion of the CT detector fabrication process is then complete and the remainder of the CT detector fabricating takes place downstream at 116.

The CT detector described with respect to FIG. 6 and fabricated according to the technique of FIG. 7 illustrates only one example of the present invention. A similar CT detector incorporating the advantages of that described with respect to FIG. 6 and fabricated in accordance with techniques different from that illustrated in FIG. 7 are contemplated and within the scope of this invention. For purpose of illustration and not limitation, additional manufacturing techniques and the resulting structures will be described with reference to FIGS. 8-10.

Figure 8:
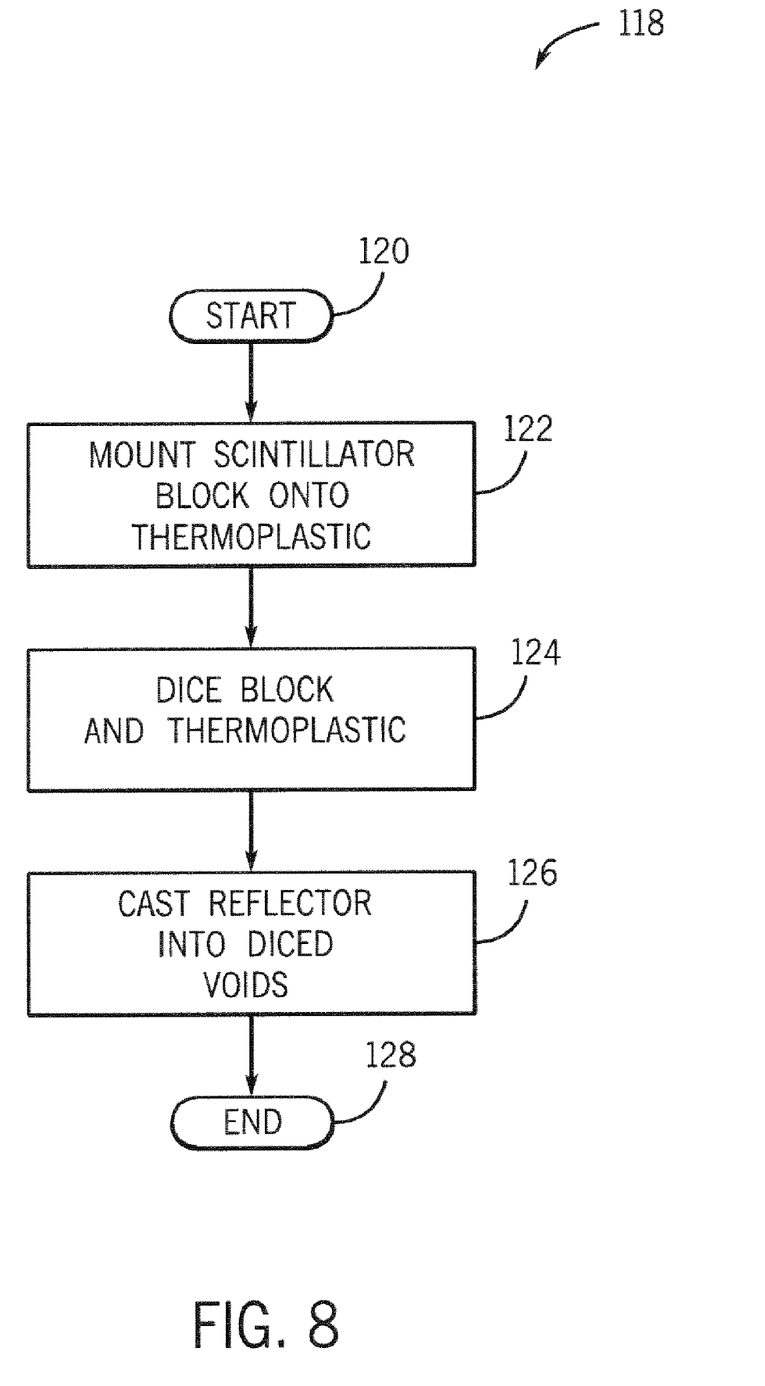
Figure 9:
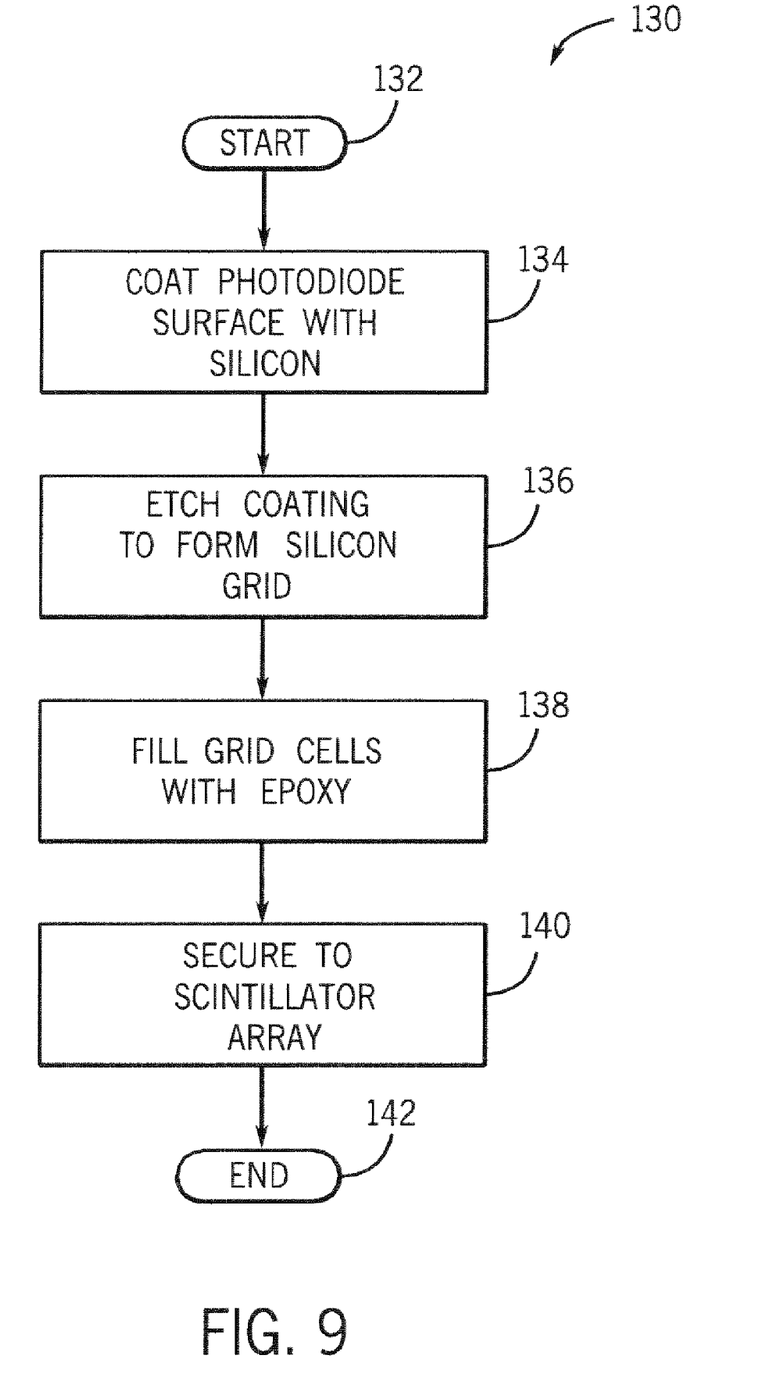

Referring now to FIG. 8, another CT manufacturing process 118 begins at 120 with a block of scintillator material being prepared. The block is then placed onto a block of thermoplastic material at 122. The scintillator block and the thermoplastic are then diced or cut 124 in accordance with known dicing processes. Preferably, only a portion of the thermoplastic is diced thereby leaving a thin, uncut portion that can be used to seal against the photodiode array. Cast reflector is then deposited in the voids 126 between scintillator cells that result from the dicing process. In contrast to the CT detector constructed in accordance with FIG. 7, an optical epoxy between the reflector plates formed by the cast reflector is not used. Because the thermoplastic material is not completely diced through, a thin thermoplastic layer results that, as discussed above, is used to secure the scintillator array to the photodiode array as opposed to an optical epoxy. Process 118 then concludes at 128 with the CT detector undergoing additional processing and fabrication in accordance with known techniques.

The processes described above involve alternations to the scintillator array. In contrast, the process of FIG. 9 creates the reflector plates by etching the photodiode array. Specifically, process 130 begins at 132 with the formation of a photodiode array. At 134, the photodiode array is coated with a film of semiconductor or other suitable materials. Preferably, a thin layer of Silicon is applied or thermally grown and allowed to cure to the photodiode light reception surface. Semiconductor materials that will not adversely affect the light collection abilities of the photodiode array should be used. The surface of the photodiode array is then masked and plasma etched at 136 using standard semiconductor fabrication techniques to form a grid. Various semiconductor fabrication processes are contemplated including chemical etching, mechanical etching, ion beam milling, and the like. The result of the etching process should result in a series of open cells defined by the semiconductor material. The open cells should be vertically aligned with the light detection surfaces of the photodiode array. The open cells are then filled with optical epoxy 138 to secure the photodiode array to the scintillator array at 140. The resulting assembly then undergoes standard post-processing techniques whereupon the process ends at 142.

Figure 10:
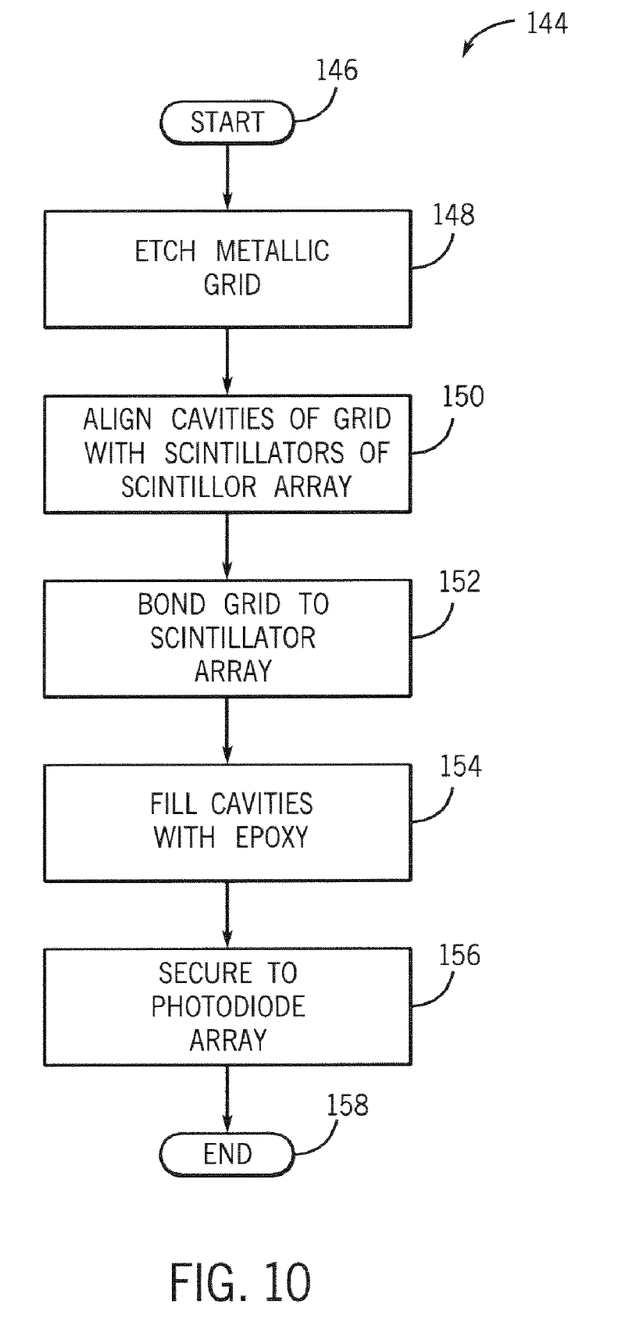

The process illustrated in FIG. 10 utilizes an intermediary element that is not integrated with the scintillator array or photodiode array. Manufacturing process 144 begins at 146 with the formation of a scintillator array and a photodiode array in accordance with known fabrication techniques. A grid is then etched at 148 from a sheet of thin metallic or other material. The grid defines a number of cells dimensionally equivalent to the scintillators and photodiodes. Additionally, the grid preferably has a height equal to the desired height of the light transmission cavities heretofore described. Accordingly, the open cells formed in the grid are aligned with the either the scintillators of the scintillator array or with the photodiodes of the photodiode array at 150. The grid is then bonded at 152 to the selected array. The open cells or cavities defined by the grid may then be filled with optical epoxy at 154. The optical epoxy is then used to secure the selected array to the other array at 156. Alternately, the open cells may be left empty and the grid bonded to the other array. The process is then complete at 158.

Each of the above-described manufacturing processes results in a CT detector having a non-contiguous optical coupler thereby avoiding the drawbacks associated with a contiguous optical coupler layer. Each of the processes produces a CT detector wherein a light transmission cavity is formed to collimate light emissions from a scintillator to a photodiode. The cavity may be filled with optical coupling epoxy or left empty and the scintillator bonded to the photodiode array. It is preferred that the cavities be filled with epoxy as this results in better optical transmission and a stronger connection being formed between the scintillator and photodiode.

Figure 11:
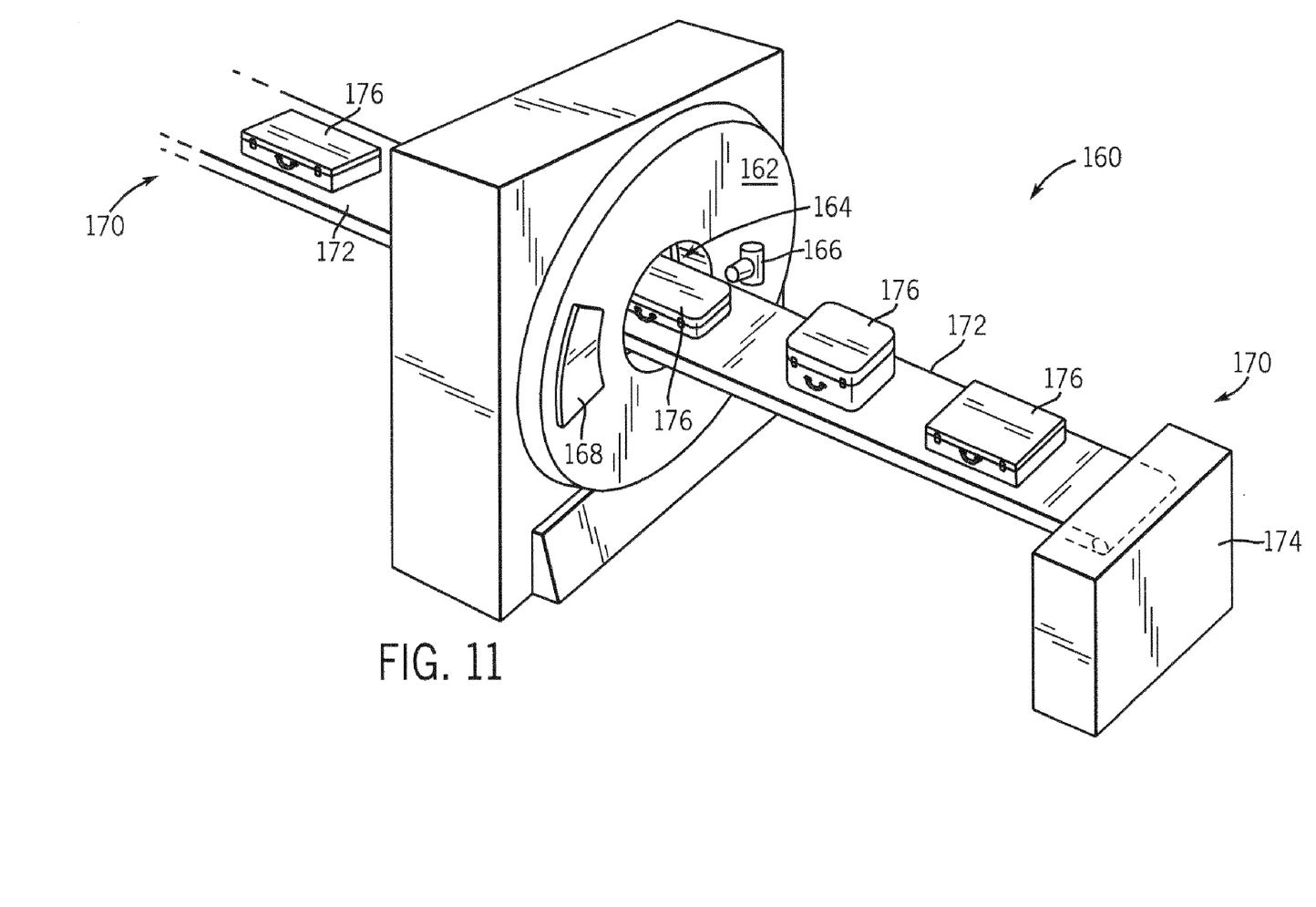
FIG. 11 is a pictorial view of a CT system for use with a non-invasive package inspection system.

Referring now to FIG. 11, package/baggage inspection system 160 includes a rotatable gantry 162 having an opening 164 therein through which packages or pieces of baggage may pass. The rotatable gantry 162 houses a high frequency electromagnetic energy source 166 as well as a detector assembly 168. A conveyor system 170 is also provided and includes a conveyor belt 172 supported by structure 174 to automatically and continuously pass packages or baggage pieces 176 through opening 164 to be scanned. Objects 176 are fed through opening 164 by conveyor belt 172, imaging data is then acquired, and the conveyor belt 172 removes the packages 176 from opening 164 in a controlled and continuous manner. As a result, postal inspectors, baggage handlers, and other security personnel may non-invasively inspect the contents of packages 176 for explosives, knives, guns, contraband, etc.

Therefore, in accordance with one embodiment of the present invention, a CT detector includes a plurality of scintillators arranged in an array to receive x-rays and output light in response to the received x-rays. A plurality of light detection elements are arranged in an array dimensionally similar to the scintillator array and are configured to detect light from the scintillators. A non-contiguous optical coupler is then used to secure the plurality of scintillators to the plurality of light detection elements.

According to another embodiment of the present invention, a CT system includes a rotatable gantry having a bore centrally disposed therein and a table movable fore and aft through the bore and configured to position a subject for CT data acquisition. A high frequency electromagnetic energy projection source is positioned within the rotatable gantry and configured to project high frequency electromagnetic energy toward the subject. The CT system further includes a detector array disposed within the rotatable gantry and configured to detect high frequency electromagnetic energy projected by the projection source and impinged by the subject. The detector array includes a plurality of scintillators arranged in a scintillator array as well as a plurality of photodiodes arranged in a photodiode array. A light collimator having a plurality of light transmission cavities is disposed between the scintillator array and the photodiode array.

In accordance with a further embodiment of the present invention, a method of CT detector manufacturing includes the steps of forming a scintillator array having a plurality of scintillators and forming a photodiode array having a plurality of photodiodes. An open-celled collimator is then deposited between the arrays. The resulting assembly is then secured to one another.

The present invention has been described in terms of the preferred embodiment, and it is recognized that equivalents, alternatives, and modifications, aside from those expressly stated, are possible and within the scope of the appending claims.

What is claimed is:

1. A CT system comprising:
   a rotatable gantry having a bore centrally disposed therein;
   a table movable fore and aft through the bore and configured to position a subject for CT data acquisition;
   a high frequency electromagnetic energy projection source positioned within the rotatable gantry and configured to project high frequency electromagnetic energy toward the subject; and
   a detector array disposed within the rotatable gantry and configured to detect high frequency electromagnetic energy projected by the projection source and impinged by the subject, the detector array including:
   a plurality of scintillators arranged in a scintillator array;
   a plurality of photodiodes arranged in a photodiode array; and
   a light collimator having a plurality of collimator plates that collectively define a plurality of light transmission cavities disposed between the plurality of scintillators and the plurality of photodiodes, the plurality of collimator plates formed of a semiconductor.

2. The CT system of claim 1 wherein the plurality of collimator plates forms a two dimensional grid.

3. The CT system of claim 1 further comprising a thin film optical coupler coupling the light collimator to the plurality of photodiodes.

4. The CT system of claim 1 wherein each light transmission cavity collimates light between a single scintillator and a single photodiode.

5. The CT system of claim 1 wherein the semiconductor is silicon.

6. The CT system of claim 5 wherein the semiconductor is thermally grown silicon.

7. The CT system of claim 1 further comprising an epoxy positioned within each light transmission cavity.

8. A CT detector comprising:
   a plurality of scintillators arranged in an array to receive x-rays and output light in response to the reception of x-rays;
   a plurality of light detection elements arranged in an array to output electrical signals in response to light detected from the plurality of scintillators; and
   a plurality of reflector elements comprising a semiconductor, the reflector elements positioned between adjacent scintillators forming a plurality of cavities that are aligned with corresponding scintillators.

9. The CT detector of claim 8 wherein the semiconductor comprises silicon.

10. The CT detector of claim 8 wherein the plurality of reflector elements have widths substantially equal to corresponding scintillators.

11. The CT detector of claim 9 wherein the silicon is thermally grown.

12. The CT detector of claim 8 further comprising an optical coupler to secure the plurality of scintillators to the plurality of light detection elements, the optical coupler positioned in the plurality of cavities and disposed between the plurality of scintillators and the plurality of light detection elements.

13. The CT detector of claim 12 wherein the optical coupler is an epoxy.

14. The CT detector of claim 8 wherein the semiconductor is etched to form the plurality of cavities.

15. The CT detector of claim 8 wherein the plurality of reflector elements forms a grid.

16. A method of manufacturing a CT detector comprising the steps of:
   forming a scintillator array having a plurality of scintillators;
   forming a photodiode array having a plurality of photodiodes;
   coating a semiconductor on a surface of the plurality of photodiodes;
   etching the semiconductor to form an open-celled collimator between the scintillator array and the photodiode array, the open-celled collimator having collimator plates extending in a direction generally parallel to x-ray transmission and having a width perpendicular to the direction generally parallel to x-ray transmission that substantially matches a width separating adjacent scintillators; and
   securing the scintillator, the open-celled collimator, and the photodiode array to one another.

17. The method of claim 16 wherein coating a semiconductor further comprises thermally growing silicon on the surface of the plurality of diodes.

18. The method of claim 16 wherein coating a semiconductor further comprises depositing silicon on the surface of the plurality of photodiodes.

19. The method of claim 16 wherein etching further comprises one of chemical etching, mechanical etching, and ion beam milling.

20. The method of claim 16 further comprising filling the open-celled collimator with an optical epoxy.

21. The method of claim 16 wherein etching further comprises etching a two dimensional grid.

* * * * *